(12) United States Patent
Pedrotti et al.

(10) Patent No.: US 6,446,384 B2
(45) Date of Patent: Sep. 10, 2002

(54) ELECTRIC EXHALER FOR THE VAPORIZATION OF DISINFESTING INSECTICIDE PRODUCTS

(75) Inventors: Andrea Pedrotti, Cavedine; Fabrizio Giorgione, Mattarello; Walter Sordo, Trento, all of (IT)

(73) Assignee: Zobele Industrie Chimiche S.p.A., Trento (IT)

( * ) Notice: Subject to any disclaimer, the term of this patent is extended or adjusted under 35 U.S.C. 154(b) by 0 days.

(21) Appl. No.: 09/870,508

(22) Filed: Jun. 1, 2001

(30) Foreign Application Priority Data

Jun. 1, 2000 (IT) ...................................... MI2000A1226

(51) Int. Cl.$^7$ ............................................. A01M 13/00
(52) U.S. Cl. ........................................ 43/129; 392/390
(58) Field of Search .................. 43/129, 138; 392/386, 392/324, 403, 390, 394, 395, 391, 392; 219/543, 544, 546, 547, 548

(56) References Cited

U.S. PATENT DOCUMENTS

| | | | | |
|---|---|---|---|---|
| 4,391,781 A | * | 7/1983 | van Lit | 422/125 |
| 5,222,186 A | * | 6/1993 | Schimanski et al. | 392/395 |
| 5,400,969 A | * | 3/1995 | Keene | 239/136 |
| 5,402,517 A | * | 3/1995 | Gillett et al. | 392/386 |
| 5,796,914 A | * | 8/1998 | Gatzemeyer et al. | 392/390 |
| 6,085,026 A | * | 7/2000 | Hammons et al. | 392/390 |
| 6,144,801 A | * | 11/2000 | Lehoux et al. | 392/390 |
| 6,236,807 B1 | * | 5/2001 | Ruffolo et al. | 392/390 |
| 6,249,645 B1 | * | 6/2001 | Smith | 392/403 |

FOREIGN PATENT DOCUMENTS

| | | |
|---|---|---|
| GB | 2 302 507 A | 1/1997 |
| WO | 98/46283 | 10/1998 |

* cited by examiner

*Primary Examiner*—Charles T. Jordan
*Assistant Examiner*—Danielle Rosenthal
(74) *Attorney, Agent, or Firm*—Young & Thompson

(57) ABSTRACT

An electric exhaler for the vaporization of disinfesting insecticide products comprises a heating resistance (R) and a refill of porous ceramic material (S) impregnated with an active substance apt to be evaporated at high temperature. The resistance (R) is apt to reach a surface temperature of at least 500° C. and the ceramic refill (S) is positioned in tight contact therewith. Preferably, the resistance (R) is cylindrical and the refill (S) has a cross-section having a Ω- or C-shape, the curved portion of which has an inner radius corresponding to the outer radius of the resistance

18 Claims, 1 Drawing Sheet

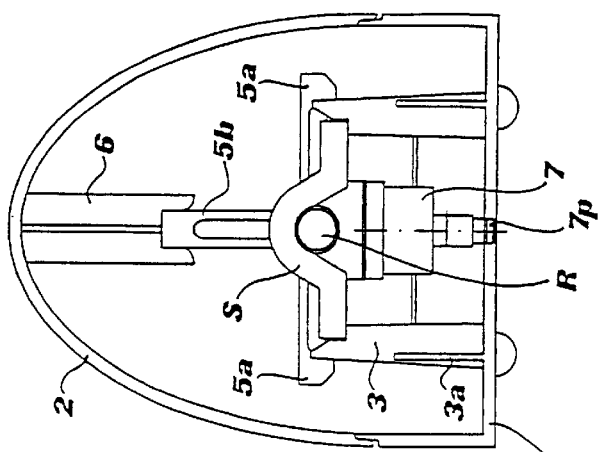
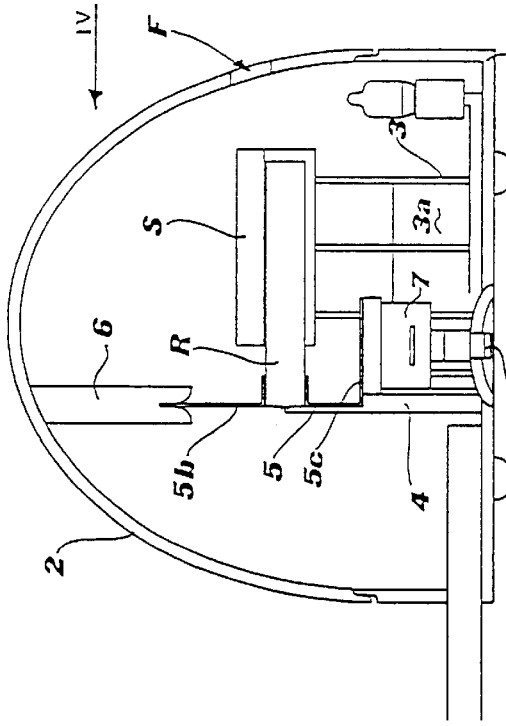
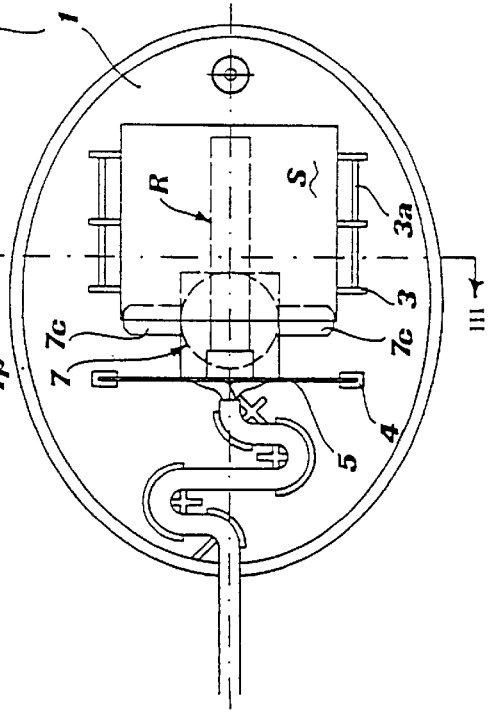
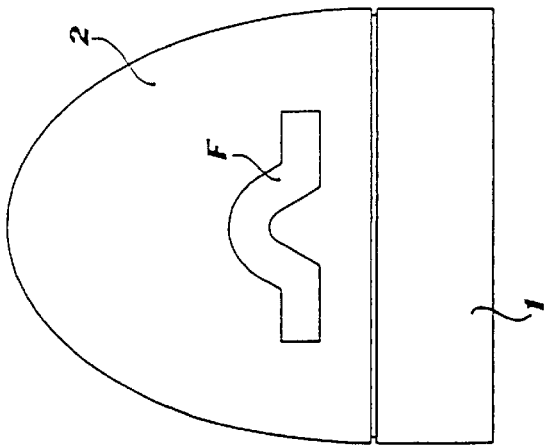

ELECTRIC EXHALER FOR THE VAPORIZATION OF DISINFESTING INSECTICIDE PRODUCTS

FIELD OF THE INVENTION

The present invention concerns an electric exhaler for the vaporization, at high temperature, of disinfesting insecticide products.

BACKGROUND OF THE INVENTION

The thorough disinfestation of closed environments from infesting insects (beetles, spiders, flies, ticks, fleas and other insects), which may nest inside houses and other closed spaces, has up-to-date been carried out by spreading into said environments suitable insecticide substances, in such concentrations as to prove effective also against insects of a certain size such as those mentioned hereabove.

For the disinfesting operation to prove really effective the rooms must be perfectly closed, any objects which will subsequently get in contact with human beings will have to be previously removed therefrom (or be carefully washed after the operation) and, finally, any furniture and cupboards in the room will have to be left open, so that the active substance may easily penetrate therein. After the active substance has been spread into the rooms having to be disinfested, it is then necessary to allow it to act for a sufficiently long period of time—for example, a couple of hours—without introducing any changes of air and obviously preventing any persons or animals from getting into such rooms during this period of time.

Two different technologies are adopted nowadays to spread the active substance into the environments having to be disinfested, and precisely, burning a combustible support impregnated with the active substance, or spreading into the environment a finely vaporized active substance by means of a suitable gaseous propellant. Both these technologies forcedly require the use of disposable containers, which cannot be used again and, furthermore, they imply introducing into the environment substances which are alien to the disinfesting action, such as the combustion gases of the support or, respectively, the gaseous propellants used to vaporize the active substance. This involves a considerable increase in the cost of such devices, compared to the intrinsic value of the mere active substance, both due to the cost of the container (higher in the case of the container holding the gaseous propellant) and due to the cost of the combustible support or of the propellant.

A further drawback of the known devices lies moreover in the fact that the alien substance introduced into the environment is apt to create both ecological problems—as it still happens nowadays in the case of several propellants, though to a reduced extent in respect of a recent past—and problems of persistent unpleasant smells or fouling, as it may happen instead in the case of combustible products which, if not used with the due care, may besides involve a slight but not totally neglectable risk of causing fires or damages to the surface coverings.

It should finally be underlined that the fumigating combustion products are actually those which prove to be more effective in use since, due to the high temperatures reached during combustion of the support, they allow a fast vaporization of the active substance used (Tetramethrin, Permethrin, Cypermethrin, Thralometrin, and the like), which normally has a rather low vapor pressure. This causes, in the environment being treated, the forming of a high initial concentration of active substance, which thus proves to be particularly effective in killing the insects present therein. Due to the aforecited drawbacks, tied to the use of combustion products, it has more recently been deemed to change over to those making use of a gaseous propellant (normally a compressed liquefied gas), which are no doubt easier to use and potentially involve less problems for the environment being treated, but which still involve the possible dangers tied to the use and storage of inflammable aerosol products (the propellant) close to heat sources, free flames and the like.

The object of the present invention is to thus supply a device for the fast vaporization of insecticide active substances, to disinfest closed environments, apt to overcome the above drawbacks while proving to be as highly effective in use as the fumigating combustion products.

OBJECT OF THE INVENTION

In particular, the object of the present invention is to supply a device for the vaporization of disinfesting products, which does not make use of disposable containers and which hence involves, for each treatment, only the reduced cost for the refill of the active substance, which does not cause the inlet into the environment of substances alien to the required active substance, which allows the fast vaporization of a high quantity of active substance, and which involves no risks of causing fires or anyhow damaging the environments in which it is used, even failing any special precautions in the use thereof.

SUMMARY OF THE INVENTION

According to the present invention, said objects are reached by means of an electric exhaler for the vaporization of disinfesting insecticide products, of the type comprising a heating element and a porous support impregnated with an active substance apt to be evaporated at high temperature, characterized in that said heating element is a resistance apt to reach a surface temperature exceeding 400° C., and preferably of 600° C., and in that said support is a refill of porous ceramic material.

According to a characteristic of the invention, the ceramic refill impregnated with the active substance is positioned adjacent to said resistance and, preferably, in contact therewith.

According to another characteristic of the invention, the ceramic refill comprises a central portion, in tight contact with the resistance and partially surrounding the same, and a peripheral portion consisting of one or more wings projecting from said central portion to rest the ceramic refill onto the structure of the electric exhaler.

BRIEF DESCRIPTION OF THE DRAWINGS

Further characteristics and advantages of the electric exhaler according to the present invention will anyhow be more evident from the following detailed description of a preferred embodiment thereof, given with reference to the accompanying drawings, in which:

FIG. 1 is a plan view of the electric exhaler according to the present invention, without the covering cap;

FIG. 2 is a longitudinal section view of the electric exhaler, along the line II—II of FIG. 1;

FIG. 3 is a cross section view of the electric exhaler, along the line III—III of FIG. 1; and FIG. 4 is a side elevation of the electric exhaler, along the direction of the arrow IV in FIG. 2, which illustrates the inlet slit for the refill of the active substance.

DETAILED DESCRIPTION OF THE INVENTION

The drawings illustrate an electric exhaler according to the present invention, having an elliptical shape in a plan view, and comprising a base 1 carrying the different elements of the electric exhaler, and a covering cap 2 apt to be fixed to the base 1 by snapping, with hooks, by screwing, or other known systems. Both the base 1 and the cap 2 are provided with holes, gratings or slits (not shown) to let through the air and, respectively, the disinfesting products. From the base 1 project a plurality of thin vertical rods 3, connected together by narrow stiffening walls 3a, as well as lower supports 4 to support the horizontal arms 5a of a metallic heatsink 5. To make the ensemble of the device more steady, the heatsink 5 may also comprise a vertical arm 5b, extending from the middle of the arms 5a and fitting into an upper support 6 fixed to the cap 2. The vertical rods 3, as well as the lower supports 4 and the support 6 are preferably formed in one piece with the base 1, or respectively with the cap 2, by injection molding of a suitable heat-resisting plastic material.

A bimetallic thermostat 7, inserted into the electric circuit feeding the resistance R by means of conductors 7c, is moreover fixed to the base 1, said thermostat 7 being of the manual resetting type, apt to be operated by means of a push-button 7p positioned into a suitable recess of the base 1 so that its movement may not interfere with the bearing surface of the electric exhaler. Alternatively, the thermostat may be of the so-called "self-hold" type, namely a bimetallic thermostat in which the cutoff of the primary electric circuit, determined by the heating of the bimetal, causes the make of a electric circuit, determined by the heating of the bimetal, causes the make of a secondary electric circuit equipped with a small resistance for heating the bimetal, so that said bimetal may remain in the position corresponding to the cutoff of the primary circuit, up to the external interruption of the power supply. A flat square element 5c of the heatsink 5 bears in contact with the top surface of the thermostat 7, said square element being apt to transfer heat to the thermostat, as better explained hereinafter. The resistance R is finally fixed overhanging from the central portion of the heatsink 5 and, more precisely, at the intersection between the horizontal arms 5a and the vertical arm 5b. Said resistance is preferably a cylindrical resistance of about 40 W, whose power is thus far higher than that (3–6 W) of the resistances normally provided in the electric heaters for the vaporization of insecticide substances for domestic use.

Said high power is required for the resistance R to promptly reach a fairly high surface temperature—for instance, at least higher than 400° C.—such as to cause the fast and strong vaporization of the active substance, which is indispensable to drive out of their nest and rapidly and efficiently destroy all the insects present in the rooms undergoing the treatment. The surface temperature reached by the resistance R will preferably exceed 500° C., and will optimally be of 600° C. The high temperature reached by the resistance R obviously creates the problem of prearranging an adequate support for the same, so as to avoid locally overheating the base 1 above the limit of mechanical strength of the plastic material forming the same. For this purpose, the special structure of the metallic heatsink 5 has been conceived, to allow providing a steady support for the resistance R and a simultaneous fast elimination of the heat transmitted thereby, so that the ends of the horizontal arms 5a, supported by the lower supports 4, and of the vertical arm 5b, fitted into the upper support 6, constantly keep at a temperature well below the safety limit indicated above; while the square element 5c of the heatsink 5 is apt to transfer a predetermined heat flow to the bimetallic thermostat 7. This latter is then set so as to interrupt the power supply to the resistance R after a time period of 10 to 15 minutes, sufficient to allow the vaporization of the entire content of active substance.

Alternatively, the electric exhaler can be equipped with a conventional timing device, or timer, which is apt to interrupt the power supply to the resistance R after a preset period of time, fixed or adjustable by the user.

The active substance is, as said, impregnated into a refill S of porous ceramic material. The refill S consists of a cylindrical body, whose generating lines are parallel to the axis of the resistance R, and the cross-section of which has the particular Ω-shape shown in FIG. 3. The refill S is inserted into the electric exhaler through the inlet slit F-sufficiently narrow, and shaped so as to make it impossible for a child to introduce his fingers therein—formed into the cap 2, as shown in FIG. 4, and the wings of its Ω-shape bear onto a corresponding seat formed by the vertical rods 3, while the central portion of the Ω-shape bears in tight contact with the upper part of the resistance R, thanks to the fact that the inner radius of the curved portion of said Ω-shape corresponds to the outer radius of the resistance R. Thanks to said configuration of the refill S, its central portion—being that impregnated with the active substance—is apt to promptly and efficiently absorb the heat transmitted by the resistance R with which it is in direct contact, while the wings of its Ω-shape increase their temperature far more slowly, thanks to the low thermal conductivity of the ceramic material and to the cooling action produced on said wings by the rising air stream formed inside the exhaler; consequently, the wings of the Ω-shape never reach such a high temperature as to create problems of mechanical resistance for the rods 3 of plastic material.

The low thermal conductivity of the ceramic refill S is further increased thanks to the fact that said refill, as seen, is entirely porous. In fact said porosity, required in the central portion of the refill S to allow impregnating the active substance, is provided also on the wings of its Ω-shape so as to reduce even further the coefficient of thermal conductivity of the ceramics, slowing down the heat transfer from the central portion to the peripheral portion of the refill S. The removal of the exhausted refill, at the end of the treatment, involves no problems and can be simply obtained by tilting sideways the electric exhaler. Since, in fact, the treatment period of about two hours is always much longer than the operating time of the electric exhaler— which may vary from a minimum of a few minutes to a maximum of about thirty minutes—by the time the operator reaches the electric exhaler, the exhausted refill has become totally cold.

According to an alternative embodiment of the present invention, the refill S still consists of a cylindrical body whose generating lines are parallel to the axis of the resistance R, but the cross-section of the support has a C-shape, the inner radius of the C-shape corresponding to the outer radius of the resistance R. In this case, the refill S thus has no bearing wings and is entirely supported by the resistance R, onto which it fits perfectly.

From the previous description it is clearly evident how the electric exhaler according to the present invention has fully reached the intended objects. To start with, the aforedescribed device involves in fact a very limited cost, only slightly higher than that of the known devices but, unlike these last ones, it can be used an indefinite number of times. For each disinfesting treatment, the material used up simply consists of the ceramic support into which is impregnated the active substance, the cost of which is thus totally negligible. The insect-killing treatment is carried out through the heat supplied by the resistance, and this provides the considerable advantage to avoid introducing into the environment combustion products or propellants—typical of the known type devices—and to also prevent any risks of fire, tied to the use of combustible products. The special configuration of the refill of ceramic material and its positioning onto the resistance allow furthermore—also thanks to the high power of said resistance—to obtain a very fast heating of the actual refill and, consequently, an equally fast and strong vaporization as that obtained with the known systems adopted at present.

The electric exhaler according to the present invention has been described with particular reference to a preferred embodiment thereof, but it is evident that the protection scope of the invention is not limited to said embodiment, but extends to any possible variants within reach of a person skilled in the art, provided that they fall within the definitions given in the following claims.

What is claimed is:

1. Electric exhaler for the fast vaporization of a disinfesting insecticide active substance having a low vapor pressure, comprising a heating resistance (R) adapted a to reach a surface temperature of at least 400° C. and a refill (S) of porous ceramic material impregnated with said active substance, said resistance (R) having the shape of a straight cylinder and said ceramic refill (S) being a cylindrical body whose generating lines are parallel to the axis of the resistance (R) and the cross-section of which has an Ω-shape, the resistance (R) and the ceramic refill (S) being so mutually positioned that a first central portion of said ceramic refill is in contact with the resistance (R) and partially surrounds the resistance and a second, pheripheral, portion of said ceramic refill has at least one wing projecting from said first portion, to rest the ceramic refill (S) on the structure of the electric exhaler.

2. Electric exhaler as in claim 1, wherein the inner radius of the curved portion of said Ω-shape corresponds to the outer radius of the resistance (R).

3. Electric exhaler as in claim 1, wherein said ceramic refill (S) bears, with the wings of its Ω-shape, on a plurality of vertical rods (3) projecting from the base (1) of the electric exhaler and formed, in one piece therewith, of a heat-resisting plastic material.

4. Electric exhaler as in claim 1, wherein said resistance (R) is fixed to the central portion of a metallic heatsink (5) having arms (5a, 5b) which are fixed to the structure of the electric exhaler.

5. Electric exhaler as in claim 4, wherein the arms (5a, 5b) of the metallic heatsink (5) are fixed to supports (4, 6) projecting from a base (1) or cap (2) of the electric exhaler and formed, in one piece therewith, of a heat-resisting plastic material.

6. Electric exhaler as in claim 4, wherein a portion (5c) of said metallic heatsink (5) is associated with a bimetallic thermostat (7), so as to transfer to said thermostat part of the heat transmitted by said resistance (R).

7. Electric exhaler as in claim 6, wherein said bimetallic thermostat (7) is adapted to interrupt the power supply to the resistance (R) after a preset period of operating time of said resistance.

8. Electric exhaler as in claim 6, wherein said bimetallic thermostat (7) is manually resettable or self-holding.

9. Electric exhaler for the fast vaporization of a disinfesting insecticide active substance having a rather low vapor pressure, comprising a heating resistance (R) adapted to reach a surface temperature of at least 400° C. and a refill (S) of porous ceramic material impregnated with said active substance, said resistance (R) having the shape of a straight cylinder and said ceramic refill (S) being a cylindrical body whose generating lines are parallel to the axis of the resistance (R) and the cross-section of which has a C-shape the inner radius of which corresponds to the outer radius of said resistance (R), the ceramic refill (S) being fitted onto the resistance (R) so as to be entirely supported thereby.

10. Electric exhaler as in claim 9, wherein said resistance (R) is fixed to a central portion of a metallic heatsink (5) having arms (5a, 5b) which are fixed to the structure of the electric exhaler.

11. Electric exhaler as in claim 10, wherein the arms (5a, 5b) of the metallic heatsink (5) are fixed to supports (4, 6) projecting from a base (1) or cap (2) of the electric exhaler and formed, in one piece therewith, of a heat-resisting plastic material.

12. Electric exhaler as in claim 10, wherein a portion (5c) of said metallic heatsink (5) is associated with a bimetallic thermostat (7), so as to transfer to said thermostat part of the heat transmitted by said resistance (R).

13. Electric exhaler as in claim 12, wherein said bimetallic thermostat (7) is adapted to interrupt the power supply to the resistance (R) after a preset period of operating time of said resistance.

14. Electric exhaler as in claim 12, wherein said bimetallic thermostat (7) is manually resettable or self-holding.

15. Electric exhaler for the vaporization of disinfesting insecticide products, comprising a heating element and a porous support impregnated with an active substance adapted to be evaporated at high temperature, said heating element being a resistance (R) adapted to reach a surface temperature of at least 400° C., said support being a refill (S) of porous ceramic material, said resistance (R) being fixed to a central portion of a metallic heat sink (5) having arms (5a, 5b) which are fixed to the structure of the electric exhaler, said arms of the metallic heat sink (5) being fixed to supports (4, 6) projecting from a base (1) or cap (2) of the electric exhaler and formed, in one piece therewith of a heat-resisting plastic material.

16. Electric exhaler for the vaporization of disinfesting insecticide products, comprising a heating element and a porous support impregnated with an active substance adapted to be evaporated at high temperature, said heating element being a resistance (R) adapted to reach a surface temperature of at least 400° C., said support being a refill (S) of porous ceramic material, said resistance (R) being fixed to a central portion of a metallic heat sink (5) having arms (5a, 5b) which are fixed to the structure of the electric exhaler, a portion (5c) of said metallic heat sink (5) being associated with a bi-metallic thermostat (7), so as to transfer to said thermostat part of the heat transmitted by said resistance (R).

17. Electric exhaler as claimed in claim 16, wherein said bi-metallic thermostat (7) is adapted to interrupt the power supply to the resistance (R) after a preset of operating time of said resistance.

18. Electric exhaler as claimed in claim 15, wherein said bi-metallic thermostat (7) is manually resettable or self-holding.

* * * * *